United States Patent [19]

Bank

[11] Patent Number: 5,126,468

[45] Date of Patent: Jun. 30, 1992

[54] CATALYSTS FOR ADDITION OF SILICON HYDRIDES TO α,β-UNSATURATED OLEFINIC NITRILES

[75] Inventor: Howard M. Bank, Freeland, Mich.

[73] Assignee: Dow Corning Corporation, Midland, Mich.

[21] Appl. No.: 737,294

[22] Filed: Jul. 29, 1991

[51] Int. Cl.$^5$ ................................................ C07F 7/10
[52] U.S. Cl. .................................................... 556/415
[58] Field of Search ......................................... 556/415

[56] References Cited

U.S. PATENT DOCUMENTS

| | | | |
|---|---|---|---|
| 2,860,153 | 11/1958 | Saam | 556/415 |
| 2,906,764 | 9/1959 | Jex et al. | 556/415 |
| 2,971,970 | 2/1961 | Bluestein | 556/415 |
| 2,971,972 | 2/1961 | Bluestein | 556/415 |

OTHER PUBLICATIONS

Rajkumar et al., Organometallics 8:549–550, 1989.
Svoboda et al., Collection Czechoslov. Chem Commun. 38:3834–3836, 1973.

*Primary Examiner*—Paul F. Shaver
*Attorney, Agent, or Firm*—William F. Boley

[57] ABSTRACT

The present invention is a process for the preparation of hydrolyzable β-cyanoalkylsilanes. More particularly, this invention relates to the catalytic addition of hydrolyzable silicon hydrides to α,β-unsaturated olefinic nitriles to form β-cyanoalkylsilanes. The instant process employs novel catalysts comprising a diamine and non-activated copper, selected inorganic copper compounds, or di-coordinate organic copper compounds.

34 Claims, No Drawings

CATALYSTS FOR ADDITION OF SILICON HYDRIDES TO α,β-UNSATURATED OLEFINIC NITRILES

BACKGROUND OF THE INVENTION

The present invention is a process of the preparation of hydrolyzable β-cyanoalkylsilanes. More particularly, this invention relates to the catalytic addition of silicon hydrides to α,β-unsaturated olefinic nitriles to form β-cyanoalkylsilanes. The instant process employs novel catalysts comprising a diamine and non-activated copper or a copper containing compound.

Hydrolyzable β-cyanoalkylsilanes are useful for the production of polyorganoxiloxanes containing the β-cyanoalkyl substituent. The silicon-bonded β-cyanoalkyl radical is extremely resistant to hydrolysis and cleavage under hot, humid conditions. Therefore, the β-cyanoalkylsilanes find particular use in the preparation of polyorganosiloxanes which must be subjected to hot humid conditions. The presence of the silicon-bonded β-cyanoalkyl radical substituted on polyorganosiloxanes also tends to stabilize the polyorganosiloxanes against swelling induced by liquid hydrocarbons.

Bluestein, U.S. Pat. No. 2,971,970, issued Feb. 14, 1961. describes a method for forming cyanoalkylsilanes. The method comprises reacting a hydrolyzable silicon hydride with an α,β-unsaturated olefinic nitrile in the presence of a diamine and a cuprous compound selected from the class consisting of cuprous oxide and cuprous halides.

Rajkumar et al.. Organometallics 8, 550-552, 1989, describes a two-component catalyst, consisting of cuprous oxide and tetramethylethylenediamine, that promotes β-hydrosilylation of acrylonitrile.

Svoboda et al.. Collection Czechoslov. Chem. Commun. 38, 3834-3836, 1973, describes binary systems of a copper compound (Cu(I) oxide. Cu(I) chloride, and Cu(II) acetylacetonate) and an isocyanide (tert-butyl or cyclohexyl isocyanide) as effective catalysts for hydrosilylation of acrylonitrile by trichlorosilane and methyldichlorosilane.

The present process employs novel catalysts, comprising a diamine and non-activated copper or selected classes of copper compounds, which promote the β-hydrosilylation of unsaturated olefinic nitriles by silicon hydrides.

SUMMARY OF INVENTION

The present invention is a process for the preparation of hydrolyzable β-cyanoalkylsilanes. More particularly, this invention relates to the catalytic addition of hydrolyzable silicon hydrides to α,β-unsaturated olefinic nitriles to form β-cyanoalkylsilanes. The instant process employs novel catalysts comprising a diamine and non-activated copper, selected inorganic copper compounds, or di-coordinate organic copper compounds.

DESCRIPTION OF INVENTION

The present invention is a process for preparation of β-cyanoalkylsilanes of formula:

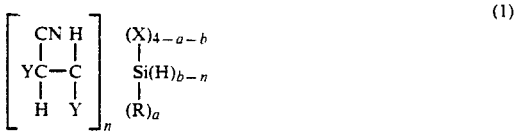

The instant process comprises contacting a silicon hydride of formula $$R_aH_bSiX_{4-a-b} \quad (2)$$

with an unsaturated olefinic nitrile of formula

in the presence of a catalyst comprising a diamine of formula $$R^1R^2NR^3NR^2_2 \quad (4)$$

with non-activated copper, selected inorganic copper compounds, or di-coordinate organic copper compounds; where each R is independently selected from a group consisting of monovalent hydrocarbon radicals substituted monovalent hydrocarbon radicals, alkoxy radicals, and aryloxy radicals; $R^1$ is a lower alkyl radical; $R^2$ is selected from a group consisting of hydrogen, lower alkyl radicals, aminoalkyl radicals, alkylaminoalkyl radicals, dialkylaminoalkyl radicals, and mixtures thereof; $R^4$ is an unsubstituted bivalent radical selected from a group consisting of alkylenes and alkenylenes of less than nine carbon atoms: X is a halogen; each Y is independently selected from a group consisting of hydrogen and lower alkyl radicals of 1 to 8 carbon atoms; n=1, 2, or 3; a=0, 1, or 2; b=1, 2, or 3; and a+b=1, 2, or 3.

In carrying out the reaction of the present invention, the unsaturated olefinic nitrile, the silicon hydride and the catalyst mixture are contacted in a suitable reaction vessel. The type of reaction vessel is not critical. The reaction can be run as a batch or as a continuous process. The process can be run under heterogeneous or homogeneous conditions. A preferred process is where the reaction is conducted in a continuous flow pressure coil.

The time required for effecting the reaction varies depending on the particular reactants, the particular catalyst mixture employed and the temperature of the reaction. In general, reaction times of 0.2 to 18 hours have been found useful. Preferred are reaction times of about 0.5 to three hours.

The temperature for conducting the process may be within a range of about 0° C. to about 200° C. It is preferred that the temperature be within a range of about 50° C. to about 150° C. Generally, higher temperatures allow the use of a catalyst mixture with a lower copper concentration, but at temperatures above about 150° C. undesired by-products may be produced.

The silicon hydride. Formula 2, employed in the present invention can contain from one to three silicon-bonded hydrogens and from one to three silicon-bonded halogen atoms. The halogen atom. X. can be selected from the group consisting of fluoride, chloride, bromide and iodide. The preferred halogen atom is chloride.

The silicon hydride can contain up to two radicals, R, selected from a group comprising monovalent hydrocarbon radicals, alkoxy radicals, aryloxy, and substituted monovalent hydrocarbon radicals, where R is inert with respect to the addition reaction. The radical, R, can be, for example, alkyl radicals, e.g.. methyl, ethyl, butyl, octyl, and octadecyl. The preferred alkyl is when R is a lower alkyl radical containing from 1 to 8 carbon atoms. The radical, R, can be, for example aryl radicals, e.g. phenyl, naphthyl, diphenyl, tolyl, xylyl, and ethylphenyl. The preferred aryl radical is phenyl. The radical, R, can be. for example: aralkyl. e.g., benzyl and phenylethyl; haloaryl, e.g., chlorophenyl, dibromophenyl and chloronaphthyl: cyanoalkyl, e.g., $\beta$-cyanoethyl, $\beta$-cyanopropyl, and $\beta$-cyanobutyl; cycloalkyl; e.g.. cyclohexyl and cycloheptyl; alkenyl, e.g.. vinyl and allyl: substituted alkyl, e.g. 3,3,3-trifluoropropyl; alkoxy, e.g. methoxy, ethoxy, and propoxy: and aryloxy, e.g. phenoxy. The most preferred radical, R, is methyl. The preferred silicon hydride is selected from a group consisting of methyldichlorosilane and trichlorosilane.

The silicon hydride is contacted with an $\alpha,\beta$-unsaturated olefinic nitrile, described by Formula 3 and containing substituents Y, where each Y is independently selected from a group consisting of hydrogen and lower alkyl radicals. By "lower alkyl radicals" is meant, alkyl radicals having from 1 to 8 carbon atoms. The unsaturated olefinic nitrile can be, for example, acrylonitrile, methacrylonitrile, crotononitrile, ethylacrylonitrile, 1-cyanobutene-1, or 2-cyanooctene-1.

The catalyst can consist of a diamine and non-activated copper or an inorganic compound of copper selected from a group consisting of non-activated copper metal. Cu(II) halide. Cu(II) oxide; copper sulfate, copper sulfide, and copper cyanide compounds: Cu(I) thiocyanide; and copper chromium compounds. The Cu(II) halide can be, for example, Cu(II) chloride, Cu(II) bromide, Cu(II) iodide, and Cu(II) fluoride. The copper sulfate can be, for example, Cu(I) sulfate and Cu(II) sulfate. The copper sulfide can be, for example. Cu(I) sulfide and Cu(II) sulfide. The copper cyanide compound can be, for example, Cu(I) cyanide and Cu(II) cyanide. The copper chromium compounds can be, for example: Cu(II) chromate, e.g., $CuCrO_4 \cdot 2CuO \cdot 2H_2O$; Cu(II) dichromate, e.g., $CuCr_2O_7 \cdot 2H_2O$; and Cu(I) chromite, e.g., $Cu_2Cr_2O_4(2CuOCr_2O_3)$.

The catalyst can comprise a diamine and a di-coordinate organic copper compound. By "di-coordinate organic copper compound" is meant compounds of general formula $Cu(R^4)_2$; where $R^4$ is a radical of formula: $—OR^5$, $—OOCR^5$,

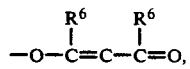

and aryl; where $R^5$ is selected from a group consisting of alkyl. alkenyl, and aryl radicals of less than 25 carbon atoms and $R^6$ is selected from a group consisting of hydrogen and hydrocarbon radicals of less than seven carbon atoms.

The di-coordinate organic copper compound can be, for example, Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) napthanate, and Cu(II) phenylate.

The diamine is as described by Formula 4, where $R^1$ is a lower alkyl radical of 1 to 8 carbon atoms: $R^2$ is selected from a group consisting of hydrogen, lower alkyl radicals of 1 to 8 carbon atoms, aminoalkyl radicals, alkylaminoalkyl radicals, dialkylaminoalkyl radicals, and mixtures thereof; and $R^3$ is an unsubstituted bivalent radical selected from the group consisting of alkylenes and alkenylenes of less than 9 carbon atoms. The diamine can be, for example, N,N,N',N'-tetramethylethylenediamine, N,N,N',N'-tetraethylethylenediamine, N,N,N'-trimethylethylenediamine, N,N-dimethyl-N',N'-diethylethylenediamine, N,N-dimethylethylenediamine, N-methyl-N,N',N'-triethylethylenediamine, N,N,N',N'',N''-pentamethyldiethylenetriamine, N,N,N'-trimethyl-N'-ethylethylenediamine, N,N',N'',N''-tetramethylmethylenediamine, N,N,N',-tetramethyldiethylenetriamine, and N-methylhexamethylenediamine. The preferred diamine is N,N,N',N'-tetramethylethylenediamine.

The catalyst comprises a mixture of the diamine with non-activated copper, selected inorganic copper compounds, or di-coordinate organic copper compounds. The mixture can be preformed and added to the reaction vessel or the diamine and elemental copper or copper compound can be added separately to the reaction vessel.

The non-activated copper metal may be added to the reactor as a particulate, for example, a powder, lumps, chips, or flakes. By "non-activated" is meant the copper particles are not pre-treated with a reducing agent or produced by reduction of a copper compound. A preferred non-activated copper is commercially available ground copper powder. Although the particle size of the non-activated copper is not critical, preferred is when the non-activated copper has a particle size less than about 325 mesh. More preferred is when the non-activated copper has a particle size less than about 100 mesh.

The catalyst may be soluble or insoluble in the reaction mixture, depending upon the silicon hydride, unsaturated olefinic nitrile, and diamine present. An organic solvent such as toluene can be added to the process if desired. However, the addition of organic solvent may reduce yield of product.

Although not necessary, it is preferred that the contents of the reactor be mixed during conduct of the instant method. Mixing of the reactor contents is especially important when the catalyst is in a particulate or insoluble form. Mixing can be accomplished by standard means, for example, mechanical stirring, refluxing, sonification, or flow turbulence.

The catalyst can comprise on a molar basis about 0.1 to 20 moles of diamine per mole of copper, the copper present either as non-activated copper or copper compound. In general, as the temperature of the process is increased a lower ratio of diamine to copper is required. A preferred mole ratio of diamine to copper is about 0.2 to 2.0.

The amount of catalyst mixture employed in relation to the amount of unsaturated olefinic nitrile may be varied within extremely wide limits. However, it is preferred to run the process under conditions where the mole ratio of copper to unsaturated olefinic. nitrile is within a range of about 0.01 to 1.0. A more preferred ratio of copper to unsaturated olefinic nitrile is in a range of about 0.08 to 0.5.

The ratio of the hydrolyzable silicon hydride to the unsaturated olefinic nitrile may be varied within wide limits. However, since the preferred process involves adding one mole of the silicon hydride to one mole of the unsaturated olefinic nitrile, in a preferred embodiment of the invention about equimolar amounts of these reactants are employed. More preferred is where the silicon hydride is present in about a ten percent molar excess in relation to the unsaturated olefinic nitrile. The use of other molar excesses of either of the two reactants is not precluded, however no particular advantage is derived.

The described method is applicable to the production of β-cyanoalkylsilanes, as described by Formula 1. The preferred β-cyanoalkylsilane, within the scope of Formula 1, is β-cyanoethylmethyldichlorosilane. However, the instant process is also applicable to the preparation of hydrolyzable silanes containing more than one silicon-bonded β-cyanoalkyl radical, for example, bis-(β-cyanoethyl)dichlorosilane and tris-(β-cyanoethyl)-chlorosilane, by the addition of one mole of silicon bi- or tri-hydride to more than one mole of unsaturated olefinic nitrile. Other examples of β-cyanoalkylsilanes that can be made by the method of this invention, within the scope of Formula 1, are: β-cyanopropyltrichlorosilane. β-cyanoethylethyldichlorosilane, β-cyanobutyloctyldichlorosilane, β-cyanoethylphenyldichlorosilane, β-cyanoethyldiphenylchlorosilane, β-cyanoethylmethylphenylchlorosilane, β-cyanoethylcyclohexyliodochlorosilane, β-cyanoethylcyclohexyliodochlorosilane, α-ethyl-β-cyanoethylmethyldichlorosilane, β-cyanoethylvinyldichlorosilane, and β-cyanoethylchlorosilane.

In order that those skilled in the art may better understand how the present invention may be practiced, the following examples are given. These examples are given for illustration and are not meant to be limiting on the instant claims.

EXAMPLE 1.

A comparative study of the ability of catalysts comprising tetramethylethylenediamine (TMEDA) and selected copper compounds to effect the addition of methyldichlorosilane to acrylonitrile to form β-cyanoethylmethyldichlorosilane was evaluated. The process was carried out in sealed tubes at a temperature of 100° C. The results of this study are presented in Table 1. The process was run by placing into each tube 0.012 mole of methyldichlorosilane and 0.01 mole of acrylonitrile. The molar ratio of copper compound to acrylonitrile (Cu/AN) and the molar ratio of TMEDA to copper compound (TMEDA/Cu) are presented in Table 1. At times presented in Table 1, the contents of individual tubes were analyzed by gas liquid chromatography using a flame ionization detector (GLC-FID).

The results are expressed as the normalized area percent of β-cyanoethylmethyldichlorosilane present (% β-CEMDS). uncorrected for response factors. Normalization of the results were effected by subtracting the area under the GLC-FID readout graph attributed to TMEDA and high boiling materials from the total area under the GLC-FID readout graph and expressing β-cyanoethylmethyldichlorosilane present as an area percent of the remaining area under the readout graph.

TABLE 1

Effect of Copper Compound on Catalyst Activity in Effecting Reaction of Methyldichlorosilane with Acrylonitrile.

| Copper Compound | Cu/AN | TMEDA/Cu | % β-CEMDS | | | |
|---|---|---|---|---|---|---|
| | | | 1 hr. | 3 hr. | 5 hr. | 18 hr. |
| Cu(II) phthalocyanine | 0.09 | 5.76 | 0.0 | — | — | 1.4 |
| $CuSO_4$ | 0.34 | 1.47 | 0.5 | — | — | 70.9 |
| CuS | 0.34 | 1.47 | 1.2 | — | — | 61.7 |
| $Cu_2S$ | 0.19 | 2.63 | 2.2 | — | 30.7 | — |
| Cu(II) napthanate | 0.07 | 7.50 | 7.6 | — | — | 33.8 |
| Cu(II) acetylacetonate | 0.06 | 8.33 | 8.0 | — | — | — |
| Cu(II) tetramethylheptanedionate | 0.08 | 6.14 | 16.4 | — | — | 37.7 |
| Cu(II) stearate | 0.04 | 13.13 | 22.3 | — | — | 81.2 |
| Cu(II) acetate | 0.34 | 1.47 | 25.3 | — | — | 84.3 |
| CuSCN | 0.34 | 1.47 | 50.3 | — | — | — |
| CuCN | 0.34 | 1.47 | 50.5 | — | — | 69.2 |
| Cu(II) methoxide | 0.34 | 1.47 | 50.5 | — | — | 82.4 |
| CuBr-dimethylsulfide | 0.34 | 1.47 | 66.9 | — | — | 62.1 |
| $CuCl_2$ | 0.34 | 1.47 | 76.0 | — | — | — |
| CuO | 0.26 | 1.92 | 78.9 | 91.6 | — | — |
| Cu chromite | 0.29 | 1.72 | 83.7 | — | — | — |
| $Cu_2O$ | 0.16 | 3.13 | 84.8 | — | 97.8 | — |
| CuCl | 0.34 | 1.47 | 91.0 | — | — | 88.4 |

EXAMPLE 2

A comparative study of the ability of catalysts comprising tetramethylethylenediamine (TMEDA) and selected copper compounds to effect the addition of trichlorosilane to acrylonitrile to form β-cyanoethyltrichlorosilane (β-CETS) was evaluated. The process was run in sealed glass tubes, at a temperature of 100° C., for three hours. Approximately 0.012 mole of trichlorosilane and 0.01 mole of acrylonitrile was added to each tube. Sufficient copper compound was added to provide a 0.12 molar ratio of Cu/AN. Sufficient TMEDA was added to each tube to provide a 1.47 molar ratio of TMEDA/Cu. Contents of each tube were analyzed by GLC using a thermal conductivity (TC) detector and the results normalized as previously described. The results are presented in Table 2. The headings of Table 2 are as previously described.

TABLE 2

Effect of Copper Compound on Catalyst Activity in Effecting Reaction of Trichlorosilane With Acrylonitrile

| Copper Compound | % β-CETS |
|---|---|
| CuS | 22 |
| CuCN | 63 |
| $CuCl_2$ | 70 |
| CuO | 73 |
| $Cu_2O$ | 75 |
| CuCl | 81 |

EXAMPLE 3.

The ability of a catalyst comprising tetramethylethylenediamine (TMEDA) and non-activated copper metal to effect the addition of methyldichlorosilane to acrylonitrile to form β-cyanoethyldichlorosilane was evaluated. Standard, commercially available, ground copper powder was employed. The process was carried out in sealed tubes at a temperature of 100° C. The results of this study are presented in Table 3. The process was run by placing into each tube 0.012 mole of methyldichlorosilane and 0.01 mole of acrylonitrile. The molar ratio of copper to acrylonitrile (Cu/AN) and the molar ratio of TMEDA to copper compound (TMEDA/Cu) are presented in Table 3. At times presented in Table 3, the contents of individual tubes were analyzed by GLC-FID and the results normalized as previously described. The results are presented in Table 3.

TABLE 3

| Effect of Copper Metal on Catalyst Activity in Effecting Reaction of Methyldichlorosilane with Acrylonitrile. | | | |
|---|---|---|---|
| Time(h) | Cu/AN | TMEDA/Cu | % β-CEMDS |
| 3 | 0.34 | 1.47 | 18.5 |
| 7.5 | 0.34 | 1.47 | 42.4 |

What is claimed is:

1. A process for preparation of β-cyanoalkylsilanes of formula

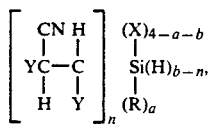

the process comprising:
contacting a silicon hydride of formula

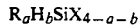

with an unsaturated olefinic nitrile of formula

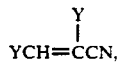

in the presence of a catalyst comprising a diamine of formula

and non-activated copper or a compound of copper selected from a group consisting of copper metal, Cu(II) halide, Cu(II) oxide; copper sulfate, copper sulfide, and copper cyanide compounds; Cu(I) thiocyanide: and copper chromium compounds; at a temperature within a range of about 0° C. to 200° C.;
where each R is independently selected from a group consisting of monovalent hydrocarbon radicals, substituted monovalent hydrocarbon radicals, alkoxy radicals, and aryloxy radicals, R¹ is a lower alkyl radical, R² is selected from a group consisting of hydrogen, lower alkyl radicals, aminoalkyl radicals, alkylaminoalkyl radicals, dialkylaminoalkyl radicals, and mixtures thereof; R³ is an unsubstituted bivalent radical selected from a group consisting of alkylenes and alkylenes of less than nine carbon atoms; X is a halide: each Y is independently selected from a group consisting of hydrogen and lower alkyl radicals of 1 to 8 carbon atoms;

n=1, 2, or 3; a=0, 1, or 2; b=1, 2, or 3; and a+b=1, 2, or 3.

2. A process according to claim 1, where contacting the silicon hydride with the unsaturated olefinic nitrile in the presence of the catalyst is effected for 0.5 hours to 3.0 hours.

3. A process according to claim 1, where the temperature is within a range of about 50° C. to 150° C.

4. A process according to claim 1, where the halide is chloride.

5. A process according to claim 1, where R is a lower alkyl radical comprised of 1 to 8 carbon atoms.

6. A process according to claim 1, where R is phenyl.

7. A process according to claim 1., where the unsaturated olefinic nitrile is acrylonitrile.

8. A process according to claim 1, where the catalyst comprises the diamine and non-activated copper.

9. A process according to claim 1, where the diamine is N,N,N',N'-tetramethylethylenediamine.

10. A process according to claim 1, where the catalyst comprises on a molar basis about 0.1 to 20 moles of diamine per mole of copper.

11. A process according to claim 1, where the catalyst comprises on a molar basis about 0.2 to 2.0 moles of diamine per mole of copper.

12. A process according to claim 1, where mole ratio of copper to unsaturated olefinic nitrile is within a range of about 0.01 to 1.0.

13. A process according to claim 1, where the ratio of copper to unsaturated olefinic nitrile is within a range of about 0.08 to 0.5.

14. A process according to claim 1, where the silicon hydride is present in about a 10 percent molar excess in relation to the unsaturated olefinic nitrile.

15. A process according to claim 1, where the β-cyanoalkylsilane is β-cyanoethylmethyldichlorosilane.

16. A process according to claim 1, where the β-cyanoalkylsilane is β-cyanoethyltrichlorosilane.

17. A process according to claim 1 where the process is carried out in a continuous flow pressure coil.

18. A process for preparation of β-cyanoalkylsilanes of formula

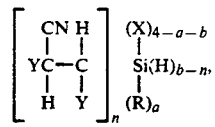

the process comprising:
contacting a silicon hydride of formula

with an unsaturated olefinic nitrile of formula

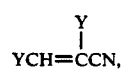

in the presence of a catalyst comprising a diamine of formula

and a di-coordinate organic copper compound; at a temperature within a range of about 0° C. to 200° C;

where each R is independently selected from a group consisting of monovalent hydrocarbon radicals, substituted monovalent hydrocarbon radicals, alkoxy radicals, and aryloxy radicals. $R^1$ is a lower alkyl radical, $R^2$ is selected from a group consisting of hydrogen, lower alkyl radicals, aminoalkyl radicals, alkylaminoalkyl radicals, dialkylaminoalkyl radicals, and mixtures thereof: $R^3$ is an unsubstituted bivalent and alkylenes of less than nine carbon atoms; X is a halide; each Y is independently selected from a group consisting of hydrogen and lower alkyl radicals of 1 to 8 carbon atoms; n = 1, 2, or 3; a = 0, 1, or 2: b = 1, 2, or 3; and a + b = 1, 2, or 3.

19. A process according to claim 18, where the di-coordinate organic copper compound is selected from a group consisting of Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) napthanate, and Cu(II) phenylate.

20. A process according to claim 18, where contacting the silicon hydride with the unsaturated olefinic nitrile in the presence of the catalyst is effected for 0.5 hours to 3.0 hours.

21. A process according to claim 18, where the temperature is within a range of about 50° C. to 150° C.

22. A process according to claim 18, where the halide is chloride.

23. A process according to claim 18, where R is a lower alkyl radical comprised of 1 to 8 carbon atoms.

24. A process according to claim 18, where R is phenyl.

25. A process according to claim 18, where the unsaturated olefinic nitrile is acrylonitrile.

26. A process according to claim 18, where the diamine is N,N,N',N'-tetramethylethylenediamine.

27. A process according to claim 18, where the catalyst comprises on a molar basis about 0.15 to 20 moles of diamine per mole of copper.

28. A process according to claim 18, where the catalyst comprises on a molar basis about 0.2 to 2.0 moles of diamine per mole of copper.

29. A process according to claim 18, where the mole ratio of copper to unsaturated olefinic nitrile is within a range of about 0.01 to 1.0.

30. A process according to claim 18, where the mole ratio of copper to unsaturated olefinic nitrile is within a range of about 0.08 to 0.5.

31. A process according to claim 18, where the silicon hydride is present in about a 10 percent molar excess in relation to the unsaturated olefinic nitrile.

32. A process according to claim 18, where the β-cyanoalkylsilane is β-cyanoethylmethyldichlorosilane.

33. A process according to claim 18, where the β-cyanoalkylsilane is β-cyanoethyltrichlorosilane.

34. A process according to claim 18, where the process is carried out in a continuous flow pressure coil.

* * * * *